United States Patent [19]

Hunston et al.

[11] Patent Number: 5,254,739
[45] Date of Patent: Oct. 19, 1993

[54] PROCESS FOR THE PRODUCTION OF CYCLOPROPYLMETHYLKETONE

[75] Inventors: Roger Hunston, Blonay; Rudolf Waditschatka, Gipf-Oberfrick, both of Switzerland

[73] Assignee: Ciba-Geigy Corporation, Ardsley, N.Y.

[21] Appl. No.: 947,658

[22] Filed: Sep. 18, 1992

Related U.S. Application Data

[63] Continuation-in-part of Ser. No. 794,536, Nov. 19, 1919.

[51] Int. Cl.$^5$ ............................................... C07C 45/67
[52] U.S. Cl. .................................................... 568/346
[58] Field of Search ........................................ 568/346

[56] References Cited

PUBLICATIONS

Takei et al., Tet. Letters, vol. 49, pp. 4389–4392 (1975).
Asaoka et al., Chemical Letters, vol. 11, pp. 1149–1152 (1975).

Primary Examiner—James H. Reamer
Attorney, Agent, or Firm—Kevin T. Mansfield; Edward McC. Roberts

[57] ABSTRACT

A process is described for the production of the known intermediate cyclopropylmethylketone which delivers a high yield, few side products, high reaction efficiency and turnover, and is more viable practically and commercially. In the presence of an excess of a Periodic Table Group I or Group II metal halide or quaternary phosphonium halide, α-acetyl-γ-butyrolactone is led continuously into a reaction vessel at 170°–200° C. and cyclopropylmethylketone distilled off continuously. The halide is recovered and recycled in the process.

26 Claims, No Drawings

PROCESS FOR THE PRODUCTION OF CYCLOPROPYLMETHYLKETONE

This is a continuation-in-part of the copending application with Ser. No. 794,536 filed Nov. 19, 1991.

The invention relates to a process for the production of cyclopropylmethylketone by heating α-acetyl-γ-butyrolactone in an inert solvent in the presence of a halide, wherein a large excess of the halide is maintained from the start to the end of the reaction.

Cyclopropylmethylketone is used as an intermediate in the manufacture of agrochemicals and pharmaceuticals as described in DE-A-3637788.

The synthesis of cyclopropylketones from acetyl-butyrolactones catalysed by an equimolar equivalent of halide ions in dipolar aprotic solvents is known. S. Takei et al. disclose in Tetrahedron Letters (49) pp.4389–92 (1975) a route to cyclopropylketone by reacting α-acetyl-γ-butyrolactone under reflux conditions of 59 hours in dimethylformamide at 160° C. in the presence of 1.1 mole equivalents NaBr whereby a yield of only 52% is obtained.

M. Asaoka et al. describe in Chemistry Letters (11) pp.1149–52 (1975) the same reaction of α-acetyl-γ-butyrolactone in hexamethylphosphoric triamide in the presence of NaI or LiCl in a molar ratio of 5:1 (corresponding to 20 mole percent NaI or LiCl) and a reaction temperature of 170° C. The cyclopropylmethylketone is removed by distillation during the reaction of 1.5 hours. The yields obtained are 86% and 42% respectively. This process is not suitable on an industrial scale due to the low amounts reacted per time unit. One disadvantage of this process is the batch-wise reaction method.

Surprisingly it was found that in the presence of a large excess of halide at any moment of the reaction, by adding continuously the α-acetyl-γ-butyrolactone (hereafter named lactone), and by removing continuously the cyclopropylmethylketone (hereafter named ketone) by distillation, there is a significant increase in the reaction efficiency and turnover, as well as a moderate increase in the yield of ketone. High yields, namely >90%, can be obtained. This reaction can be carried out continuously and on an industrial scale. The amount of halide required per unit of ketone produced is substantially reduced because the halide can be recovered and re-used.

The object of the invention is a process for the production of cyclopropylmethylketone by heating from 160° C. to 220° C. α-acetyl-γ-butyrolactone in the presence of a halide, optionally in an inert solvent, characterized in that i) the halide is selected from the group of LiCl and $MX_n$, wherein M is $Li^{\oplus}$, $Na^{\oplus}$, $K^{\oplus}$ or quaternary phosphonium when n=1, and $Mg^{2\oplus}$ or $Ca^{2\oplus}$ when n=2, and X is $Br^{\ominus}$ or $I^{\ominus}$, ii) the said acetyl-butyrolactone is added throughout the reaction continuously, and simultaneously cyclopropylmethylketone is distilled off continuously, and iii) a large excess of the halide is maintained from the start to the end of the reaction.

A preferred temperature range for the reaction is 160° C.–210° C. and the most preferred range is 170° C.–200° C.

The reaction can be carried out in an inert solvent or without solvent in the reactant itself. The inert solvent is preferably aprotic. If an alkali or an alkaline earth metal halide is used, the solvent is also preferably dipolar. If a phosphonium halide is used, the solvent can be apolar. It is advantageous for the boiling temperature of the solvent to exceed the reaction temperature by more than 20° C., preferably by more than 40° C., for example about 50° C.; in order to avoid co-distillation with the ketone, it is advantageous that the boiling point of the solvent itself exceeds 200° C.

The solvents used may be, for example: sulfones; sulfoxides; N,N-tetrasubstituted ureas; N-alkylated lactams or N-dialkylated acid amides; ethers; aliphatic, cycloaliphatic or aromatic hydrocarbons, which may be substituted with fluorine, chlorine, or $C_1$–$C_4$-alkyl; carboxylic acid esters and lactones; nitriles.

Some specific examples of solvents are:

sulfone: dimethylsulfone, diethylsulfone, tetramethylenesulfone.

sulfoxide: dimethylsulfoxide, diethylsulfoxide.

N,N-tetrasubstituted urea: N-methylethyl-N'-methylethylurea, N-dimethyl-N'-dipropylurea, tetramethylurea, tetraethylurea, N,N'-dimethyl-N,N'-1,3-propyleneurea, N,N'-dimethyl-N,N'-ethyleneurea.

N-alkylated lactam: N-methylpyrrolidone, N-ethylpyrrolidone.

N-dialkylated acid amide: N-dimethylformamide, N-diethylformamide, N-dimethylacetamide.

ether: polyethylglycolether, diethylenglycoldimethylether, diethylenglycoldiethylether.

aliphatic hydrocarbon: nonane, decane cycloaliphatic hydrocarbon: decahydronaphthalene.

aromatic hydrocarbon: xylene, tetrahydronaphthalene, dichlorobenzene.

carboxylic acid ester: benzoic-methylester.

nitrile: benzonitrile, phenylacetonitrile.

Preferred solvents are N-methylpyrrolidone, tetramethylenesulfone, N,N'-dimethyl-N,N'-1,3-propyleneurea and N,N'-dimethyl-N,N'-ethyleneurea.

The quantity of solvent added is sufficient to essentially dissolve the halide. The concentration of halide in the solvent may be 1–40 volume-%, preferably 2–30 volume-%, more preferably 5–25 volume-%, and most preferably 10–20 volume-%.

Examples of alkali and alkaline earth metal halides are LiCl, LiBr, LiI, NaBr, NaI, KBr, KI, $MgBr_2$, $CaBr_2$, $MgI_2$ and $CaI_2$. In a preferred embodiment of the invention the reaction is carried out in the presence of alkali metal halides. Preferred alkali metal halides are NaBr and NaI. Iodides are generally preferred over bromides and the most preferred halide is NaI.

Quaternary phosphonium bromides or iodides may be employed which correspond to the formula $R_1R_2R_3R_4P^{\oplus}X^{\ominus}$ wherein $R_1$, $R_2$, $R_3$ and $R_4$ represent independently linear or branched $C_1$–$C_{20}$, cyclo alkyl of 5–8 ring carbons, phenyl or benzyl, whereby the cyclic residues are unsubstituted or substituted with $C_1$–$C_9$-alkyl or $C_1$–$C_9$-alkoxy, and X is $Br^{\ominus}$ or $I^{\ominus}$.

The cyclic residues are preferably unsubstituted or substituted with $C_1$–$C_6$-alkyl or $C_1$–$C_6$-alkoxy, for example methyl, ethyl, methoxy or ethoxy.

The groups $R_1$, $R_2$, $R_3$ and $R_4$ are preferably identical. $R_1$, $R_2$, $R_3$ and $R_4$ are preferably linear alkyl containing preferably 1–12 carbon atoms and particularly 1–6 carbon atoms, or phenyl or benzyl.

Examples of $R_1$, $R_2$, $R_3$ and $R_4$ are methyl, ethyl, and the isomers of propyl, butyl, pentyl, hexyl, heptyl, octyl, nonyl, decyl, undecyl, dodecyl, tetradecyl and octadecyl. Preferred alkyl groups are methyl, ethyl, n-propyl, i-propyl, n-butyl, i-butyl, t-butyl.

Examples of cycloalkyls are cyclopentyl and cyclohexyl. Examples of substituted phenyls and benzyls are methylphenyl, methoxyphenyl, methylbenzyl and methoxybenzyl.

Some preferred examples of phosphonium halides are: tetramethyl-, tetraethyl-, tetra-n-propyl-, tetra-n-butyl-, and methyltriphenyl- phosphonium bromide or -iodide.

The reaction can be carried out by placing in the reaction vessel the solvent, optionally the lactone, and all the halide, heating and then adding the lactone.

It is advantageous to dry and deoxygenate the solvent prior to starting the reaction. This can be accomplished as follows: after loading the solvent into the reaction vessel, same is warmed to 60°-80° C. and a vacuum applied which is broken with $N_2$. This process is repeated several times. The solvent is dried by distilling off approximately 1% by volume of the reaction mixture.

The lactone is introduced into the heated reaction vessel to the extent that, at any moment during the reaction, there are present, for example, 1–100, preferably 2–50, and more preferably 3–10 molar equivalents of halide.

The lactone is led into the vessel which has been heated to e.g. 170°-220° C. and the ketone begins to distil after saturation of the reaction mixture. The most preferred temperature range is 170°-200° C. It may be advantageous to preheat the lactone.

The lactone is added continuously during the reaction. This continuous process is a preferred embodiment of the reaction.

A particularly effective method of carrying out the continuous process is to use a thin film evaporator (TFE). The reaction mixture of halide, lactone and solvent is fed continuously onto a TFE whose surface is maintained at 180°-190° C. The ketone formed on the evaporator surface is distilled off continuously; the reaction mixture, containing unreacted lactone, is removed from the base of the TFE, the lactone concentration adjusted, and the mixture fed back into the top of the TFE.

A preferred embodiment of the process according to the invention is to distil off the product from the reaction vessel using a semi-continuous fractionation method. A distillation column consisting of a number of plates is connected to the reaction vessel and during the course of the reaction a temperature gradient is established up the column. The product may be collected in an improved quality at the plate number(s) corresponding to the boiling point range of cyclopropylmethylketone. This can be, for example, half way up the column and side products are collected lower down or higher up the column if desired, depending on their respective boiling points.

The reaction is normally carried out at atmospheric pressure, but it may also be carried out at a somewhat reduced pressure or under high pressure when lower boiling temperature solvents are used. The boiling temperature of the solvent is greater than that of the ketone produced.

The advantages of this process are as follows:
a) more efficient production rate of ketone in high yield,
b) much greater turnover of the halide,
c) few side products,
d) more facile and economic production on a commercial scale,
e) the possibility of using no solvent, thus avoiding the necessity of solvent recovery,
f) the halide can be recycled and its consumption is extremely low (less than 1%).

The halide recycling is preferably carried out as follows: the solvent is distilled off and water is added. The organic residue is removed by extraction and the solvent is re-added to the aqueous halide solution. The water is distilled off and the reaction started again.

High turnover of the halide means, for example, that during a reaction process of 100 hours, 1 molar equivalent of halide reacts with approximately 250 molar equivalents of lactone. The product is obtained in a high purity and can be used directly as an intermediate in further reactions. The process is compact, requiring few installations; a vessel volume of 2–4 $m^3$ is sufficient to produce several thousand tons of ketone in one year.

The following examples demonstrate the process of the invention.

EXAMPLES

Examples 1–10 are carried out on a laboratory scale, examples 11, 12 and 13 on a pilot plant scale.

EXAMPLE 1

100 ml dry, deoxygenated solvent and 15 g of NaI are introduced into a 300 ml round-bottomed flask equipped with a thermometer, addition funnel, distillation column, and gas-washer. The mixture is heated to 180° C. and acetylbutyrolactone is introduced at a rate of 50 g/h and $CO_2$ evolution commences immediately. After a short period, ketone distills at a rate of 30 g/h. After 100 molar equivalents of lactone have been added in relation to NaI, the introduction is stopped and the distillation of ketone allowed to finish. A yield of 775 g (92%) ketone is achieved.

Examples 2–10 are carried out in a similar manner. The following table summarises example results.

| Example No. | Solvent | Halide | Yield CPMK |
|---|---|---|---|
| 1 | NMP | NaI | 92% |
| 2 | NMP | LiBr | 85% |
| 3 | NMP | NaBr | 80% |
| 4 | DMPU | NaI | 92% |
| 5 | DMEU | NaI | 89% |
| 6 | Sulfolane | NaI | 88% |
| 7 | NMP | Bu₄PBr | 85% |
| 8 | Tetralin | Bu₄PBr | 85% |
| 9 | DMPU | LiI | 92% |
| 10 | DMPU | CaI₂ | 80% |
| 11 | NMP | NaI | 90% |
| 12 | DMPU | NaI | 90% |

Abbreviations
CPMK: cyclopropylmethylketone
NMP: N-methylpyrrolidone
DMPU: N,N'-dimethyl-N,N'-1,3-propyleneurea
DMEU: N,N'-dimethyl-N,N'-ethyleneurea
Sulfolane: tetramethylenesulfone
Tetralin: tetrahydronaphthalene
Bu: n-butyl

EXAMPLE 11

25 kg NMP are dried, deoxygenated, and 4.59 kg (30 moles) NaI are added to the vessel which is heated to 180° C. 386 kg (3000 moles) lactone are fed in constantly over 38 hours which corresponds to a rate of 10 kg/hr or 78 moles/hr. Approximately 227 kg ketone distil off over the 38 hour period.

EXAMPLE 12

25 kg DMPU and 4.59 kg (30 moles) NaI are added to the reaction vessel which is heated to 180° C. 960 kg (7500 moles) lactone are fed in constantly over 96 hours which corresponds to a rate of 10 kg/hr or 78 moles/hr, the temperature being maintained at 180° C. Approximately 580 kg ketone distil off over the 96 hour period.

The DMPU is recovered from the reaction mixture by distillation. A vacuum of 30 mbar is applied whilst maintaining a temperature of 160°-180° C. in the vessel.

Recovery of the halide

The NaI is recovered from the residue after solvent distillation by cooling the vessel to 60° C. and adding 25 kg water and 15 kg toluene. The aqueous NaI solution is separated from the organic solution and the NaI recovered after distillation of the water.

Recycling the halide

The NaI solution is returned into the reactor, and, whilst the DMPU (recovered) is returned into the same reactor, the water is removed by distillation. When the system is anhydrous, the addition of the lactone can be recommenced.

EXAMPLE 13

258 kg DMPU and 46 kg (300 moles) NaI are added to the reaction vessel which, after de-oxygenation, is heated to 180° C. 7670 kg (59,860 moles) lactone are fed in over 96 hours while the temperature is maintained at 180° C. After a constant temperature gradient is established in the column, approximately 4625 kg of ketone of 98% quality are drawn off about half way up the column, at the point corresponding to the boiling point of the ketone.

The DMPU is recovered from the reaction mixture by distillation and the NaI is recovered from the residue by extraction.

We claim:

1. A process for the production of cyclopropylmethylketone by heating from 160° C. to 220° C. α-acetyl-γ-butyrolactone in the presence of a halide, optionally in an inert solvent, characterized in that i) the halide is selected from the group of LiCl and $MX_n$, wherein M is $Li^\oplus$, $Na^\oplus$, $K^\oplus$ or quaternary phosphonium when n=1, and $Mg^{2\oplus}$ or $Ca^{2\oplus}$ when n=2, and X is $Br^\ominus$ or $I^\ominus$, ii) the said acetylbutyrolactone is added throughout the reaction continuously and simultaneously cyclopropylmethylketone is distilled off continuously, and iii) a large excess of the halide is maintained from the start to the end of the reaction.

2. A process according to claim 1, characterized in that the halide is the bromide or iodide of Na.

3. A process according to claim 1, characterized in that the halide is $CaI_2$.

4. A process according to claim 1, characterized in that the quaternary phosphonium halide corresponds to the formula $R_1R_2R_3R_4P^\oplus X^\ominus$ wherein $R_1$, $R_2$, $R_3$ and $R_4$ represent independently linear or branched $C_1$-$C_{20}$, cyclo alkyl of 5-8 ring carbons, phenyl or benzyl, whereby the cyclic residues are unsubstituted or substituted with $C_1$-$C_9$-alkyl or $C_1$-$C_9$-alkoxy, and X is $Br^\ominus$ or $I^\ominus$.

5. A process according to claim 4, wherein the cyclic residues are unsubstituted or substituted with $C_1$-$C_6$-alkyl or $C_1$-$C_6$-alkoxy.

6. A process according to claim 4, wherein $R_1$, $R_2$, $R_3$ and $R_4$ represent independently $C_1$-$C_{12}$-alkyl.

7. A process according to claim 1, characterized in that the halide is essentially dissolved in the inert solvent.

8. A process according to claim 1, characterized in that the halide concentration in the solvent is between 1 and 40 volume-%.

9. A process according to claim 1, characterized in that the halide concentration in the solvent is between 2 and 30 volume-%.

10. A process according to claim 1, characterized in that the halide concentration in the solvent is between 5 and 25 volume-%.

11. A process according to claim 10, characterized in that the halide concentration in the solvent is between 10 and 20 volume-%.

12. A process according to claim 1, characterized in that the halide is present in an excess of 1 to 100 molar equivalents of acetylbutyrolactone at any moment during the reaction.

13. A process according to claim 12 where the excess is from 2 to 50 molar equivalents.

14. A process according to claim 12 where the excess is from 3 to 10 molar equivalents.

15. A process according to claim 1 where the inert solvent is aprotic.

16. A process according to claim 1, characterized in that the boiling temperature of the solvent exceeds the reaction temperature by more than 20° C.

17. A process according to claim 1 wherein the boiling point of the solvent exceeds the reaction temperature by more than 40° C.

18. A process according to claim 15 where the solvent is tetramethylenesulfone, dimethylethylurea, dimethylpropylurea, N-methylpyrrolidone, polyethylglycolether or tetrahydronaphthalene.

19. A process according to claim 1, characterized in that the temperature range for the reaction is 160° C.-210° C.

20. A process according to claim 17, characterized in that the temperature range for the reaction is 170° C.-200° C.

21. A process according to claim 1, characterized in that the reaction is carried out at atmospheric pressure.

22. A process according to claim 1, characterized in that the halide is recycled.

23. A process according to claim 22, characterized in that the solvent is distilled off, water added, the organic residue removed by extraction, the solvent re-added to the aqueous halide solution, the water distilled off and the reaction started again.

24. A process according to claim 1, characterized in that the continuous process is carried out in a reaction vessel.

25. A process according to claim 1, characterized in that the continuous process is carried out on a thin film evaporator.

26. A process according to claim 1, characterized in that a distillation column consisting of a number of plates is connected to the reaction vessel, a temperature gradient forms within said column and cyclopropylmethylketone of improved quality is collected at the plate number(s) corresponding to its boiling point range.

* * * * *